(12) United States Patent
Ganga, Sr.

(10) Patent No.: US 10,105,298 B1
(45) Date of Patent: *Oct. 23, 2018

(54) ANTIMICROBIAL SKIN CREAM

(71) Applicant: Yvon Samba Ganga, Sr., San Diego, CA (US)

(72) Inventor: Yvon Samba Ganga, Sr., San Diego, CA (US)

(*) Notice: Subject to any disclaimer, the term of this patent is extended or adjusted under 35 U.S.C. 154(b) by 136 days.

This patent is subject to a terminal disclaimer.

(21) Appl. No.: 15/363,940

(22) Filed: Nov. 29, 2016

Related U.S. Application Data

(63) Continuation-in-part of application No. 15/133,172, filed on Apr. 19, 2016, now Pat. No. 9,987,305.

(51) Int. Cl.
| | | |
|---|---|---|
| *A61K 36/00* | (2006.01) | |
| *A61K 8/26* | (2006.01) | |
| *A61Q 17/00* | (2006.01) | |
| *A61Q 19/00* | (2006.01) | |
| *A61K 8/46* | (2006.01) | |
| *A61K 8/49* | (2006.01) | |
| *A61K 8/20* | (2006.01) | |
| *A61K 8/34* | (2006.01) | |
| *A61K 8/23* | (2006.01) | |
| *A61K 8/65* | (2006.01) | |
| *A61K 8/92* | (2006.01) | |
| *A61K 8/97* | (2017.01) | |
| *A61K 8/98* | (2006.01) | |
| *A61K 8/19* | (2006.01) | |
| *A61K 8/67* | (2006.01) | |
| *A61K 8/06* | (2006.01) | |
| *A61K 8/04* | (2006.01) | |
| *A61Q 19/08* | (2006.01) | |
| *A61Q 19/10* | (2006.01) | |

(52) U.S. Cl.
CPC .............. *A61K 8/26* (2013.01); *A61K 8/042* (2013.01); *A61K 8/06* (2013.01); *A61K 8/19* (2013.01); *A61K 8/20* (2013.01); *A61K 8/23* (2013.01); *A61K 8/34* (2013.01); *A61K 8/463* (2013.01); *A61K 8/494* (2013.01); *A61K 8/65* (2013.01); *A61K 8/671* (2013.01); *A61K 8/673* (2013.01); *A61K 8/676* (2013.01); *A61K 8/678* (2013.01); *A61K 8/92* (2013.01); *A61K 8/922* (2013.01); *A61K 8/97* (2013.01); *A61K 8/988* (2013.01); *A61Q 17/005* (2013.01); *A61Q 19/00* (2013.01); *A61Q 19/08* (2013.01); *A61Q 19/10* (2013.01)

(58) Field of Classification Search
CPC ..................................................... A61K 36/00
See application file for complete search history.

(56) References Cited

U.S. PATENT DOCUMENTS

| | | | | |
|---|---|---|---|---|
| 2002/0106337 A1* | 8/2002 | Deckers | ................. | A23D 7/001 424/59 |
| 2010/0178511 A1* | 7/2010 | Letard | ................... | C07F 15/025 428/404 |

FOREIGN PATENT DOCUMENTS

| | | | | |
|---|---|---|---|---|
| DE | 10145833 A1 * | 3/2003 | ............... | A61K 8/97 |

OTHER PUBLICATIONS

Angienda et al, Potential application of plant essential oils at sub-lethal concentrations under extrinsic conditions that enhance their antimicrobial effectiveness against pathogenic bacteria. African Journal of Microbiology Research (2010), vol. 4, No. 16, pp. 1678-1684.*

* cited by examiner

*Primary Examiner* — Qiuwen Mi
(74) *Attorney, Agent, or Firm* — Plager Schack LLP; Mark H. Plager

(57) ABSTRACT

Some embodiments of the present disclosure include a cream for treating the skin. The cream may include gray clay kaolin; sodium lauryl ether sulfate; blue tartarzine; sodium chloride; menthol; metabisulfite sodium; gelatin; mineral oil; olive oil; oil of cloves; water; green tea; honey; and aloe vera. The cream may also include talc, apple perfume, vitamin E, vitamin D, vitamin C, vitamin B2, vitamin B5, vitamin H, vitamin B6, and vitamin D. The cream may also include fatty acids.

8 Claims, No Drawings

ANTIMICROBIAL SKIN CREAM

RELATED APPLICATION

This application claims priority to and is a continuation of non-provisional patent application U.S. Ser. No. 15/133,172 filed on Apr. 19, 2016, the entire contents of which is herein incorporated by reference.

BACKGROUND

The embodiments herein relate generally to skin care, and more particularly, to an antimicrobial skin cream.

The skin is the largest organ in the body, covering the surface of the human body and serving as the first line of defense in protecting the human from invasion of foreign pathogens and external injuries. In terms of wound healing, a human has the ability to self-heal a small area. However, when a person has a large area wound or poor skin restoration ability, such as those affected by diabetes, psoriasis, or leprosy, the individual may be unable to self-heal adequately, which can lead to infection.

Therefore, what is needed is a skin cream designed to improve tissue regeneration, particularly when treating skin lesions, wounds, burns, and Buruli ulcers while simultaneously having cosmetic applications as well.

SUMMARY

Some embodiments of the present disclosure include a cream for treating the skin. The cream may include gray clay kaolin; sodium lauryl ether sulfate; Brilliant blue or blue tartrazine; sodium chloride; menthol; metabisulfite sodium; gelatin; mineral oil; olive oil; oil of cloves; water; green tea; honey; and aloe vera. The cream may also include talc, apple perfume, vitamin E, vitamin D, vitamin C, vitamin B2, vitamin B5, vitamin H, vitamin B6, and vitamin D.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

The cream of the present disclosure may be used to heal and rejuvenate the skin and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

| | |
|---|---|
| 1. | Gray clay kaolin |
| 2. | Sodium lauryl ether sulfate |
| 3. | Sodium chloride |
| 4. | Menthol |
| 5. | Water |
| 6. | Honey |
| 7. | Aloe Vera |
| 8. | Vitamins |
| 9. | Gelatin |
| 10. | Oils |
| 11. | Metabisulfite Sodium |
| 12. | Talc |
| 13. | Green Tea |
| 14. | Brilliant Blue or Blue Tartrazine |

The various elements of the cream of the present disclosure may be related in the following exemplary fashion. It is not intended to limit the scope or nature of the relationships between the various elements and the following examples are presented as illustrative examples only.

By way of example, some embodiments of the present disclosure include a skin cream comprising gray clay kaolin (chemical formula $Al_2Si_2O_5(OH)_4$); sodium lauryl ether sulfate; $CH_3(CH_2)_{11}(OCH_2CH_2)_nOSO_3Na$, wherein n is 2 or 3; blue tartrazine (chemical formula $C_{16}H_9N_4Na_3O_9S_2$); salt (NaCl); menthol ($C_{10}H_{20}O$); metabisulfite sodium ($Na_2S_2O_5$); gelatin; mineral oil ($C_{102}H_{151}O_{39}N_{31}$); olive oil ($CH_3(CH_2)_7CH=CH(CH_2)_7COOH$); oil of cloves

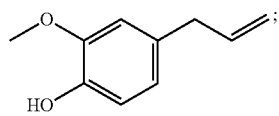

water; optionally, talc ($Mg_3Si_4O_{10}(OH)_2$); green tea; perfume, such as apple scented perfume; honey; aloe vera; optionally, oleic acid; optionally, benzoic acid; and optionally a mixture of vitamins. The fatty acids (oil of cloves, benzoic acid, and oleic acid) may have antimicrobial properties. In some embodiments, the mixture of vitamins may comprise vitamin E; vitamin D; vitamin C; vitamin B2; vitamin B5; vitamin H; vitamin B6; and vitamin D. Gray clay kaolin is a hydrous aluminum phyllosilicate and may include mineral elements, such as Fe, Mg, Na, K, Ti, Ca, and water. The $CH_3(CH_2)_{11}(OCH_2CH_2)_nOSO_3Na$ may provide for excellent decontamination, emulsification, dispersion, wetting, solubilizing performance and foaming. It may also function as a thickener with good solvency, while also having limited irritation to skin and eyes. The skin cream may have a pH of about 7.4. Additionally, the skin cream may be green in color.

A particular embodiment of the present disclosure may comprise a batch of the cream comprising about 260 kg gray kaolin clay, about 4 kg sodium lauryl ether sulfate, about 0.8 oz (or 25 g) blue tartrazine; about 2.2 kg salt (sodium chloride—NaCl), about 100g menthol; about 50 g metabisulfite sodium; about 95 kg gelatin; about 20 L mineral oil; about 25 L olive oil; about 25 L oil of cloves; about 20 L water; about 20 kg talc; about 5 L green tea; about ⅛ L perfume; about 5 L honey; about 10 L aloe vera; about 2,000 international units (IU) vitamin E; about 100,000 IU vitamin A; about 300 mg vitamin C; about 100 mg vitamin B2; about 250 mg vitamin B5; about 2.5 mg vitamin H; about 100 mg vitamin B6; and about 400 IU vitamin D. In embodiments, the cream may comprise about 60% gray kaolin clay.

The gray clay kaolin may comprise alumina silicate, calcium, magnesium, sodium, and potassium. The high silica content of the clay may result in the strengthening of the elastic tissues on the body, particularly in the case of contaminated blood.

The gelatin used in forming the cream of the present disclosure may be comprised mainly of collagen, which is a protein found in animal tissues, ligaments, tendons, bone, and skin. Thus, the gelatin may have healing properties, because it is a rich source of dietary collagen. The gelatin may also comprise proline, which is an amino acid that may help maintain a youthful appearance.

The Brilliant blue or blue tartrazine used in the cream may be a product derived from synthetic lemon yellow and is conventionally used as a food coloring.

The mineral oil included in the cream of the present disclosure may prevent water loss from the skin. In other words, it may act as a moisturizer. In some embodiments, the mineral oil may be replaced by Vaseline. The use of mineral oil may lead to an increase in stratum corneum content by reducing trans epidermal and emolliency.

To summarize, the skin cream of the present disclosure may comprise the following:

Part 1: Gray clay kaolin $Al_2(Si_2O_5)(OH)_4$

All elements listed in formula:

Al, H, 0, Si - search for minerals with similar chemistry

Common Mineral Elements: Fe, Mg, Na, K, Ti, Ca, $H_2O$

The gray clay Kaolin formula is: $(Ca,Na,H)(Al,Mg,Fe,Zn)_2(Si,Al)_4O_{10}(OH)_2*H_2O+$ sodium lauryl ether sulfate (shown below)

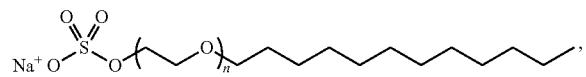

where n is 2 or 3

Part 2: sodium laureth sulfate: $CH_3(CH_2)_{10}CH_2(OCH_2CH_2)OSO_3Na$

Part 3: water, which naturally contains minerals, such as Mg, Na, Ca, Fe, and the like Part 4: Brilliant Blue $(C_{37}H_{34}N_2Na_2O_9S_3)$ or blue tartrazine $(C_{16}H_9N_{43}O_9S_2)$:

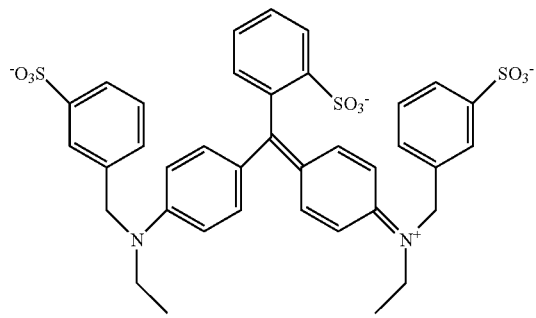

Final Product: $(Al,Zn,Fe1,67MgO,33)Si_4O_{10}(OH)_2Na^+Ca^{++})$

The weak acid character of the green clay as a Bronsted character clay arises mainly due to the dissociation of the intercalated water molecules coordinated to lauryl ether sulfate and Brilliant blue or blue tartrazine. Higher levels of Bronsted acidity are achieved when highly polarizing ions in solution have exchanged for $Na^+$, $Ca^{2+}$, in the natural clay, ions $Na^+$ present in laureth sulfate and blue tartrazine with alkali properties:

$[M(H_2O)_n]^{3+} \leftrightarrow [M(H_2O)_n-1OH]^{2+}+H^+$ (green cream clay pH=7.4)

The surface area and the pore volume in the green cream clay structure may also add to the efficiency of the catalyst. Total acidity may be further increased by proton-exchange on treating the gray clay with water, sodium laureth sulfate, and brilliant blue or blue tartrazine. As a result, a corrosive acid medium is avoided, and the clay is used as a Bronsted acid.

The interlayer in the antimicrobial green clay normally contains $Na^+$, $Ca^{2+}$, and $Mg^{2+}$ that are alkali properties as compensatory cations for the charge imbalance. When the clay is dry, these cations reside in the hexagonal cavities of the silica sheets. However, when the clay is treated with water, lauryl ether sulfate, and blue tratarzine, the cations may relocate themselves in the interlamellar region and become exchangeable by a variety of both metallic and non metallic cations, such as $H_3O^+$, $Al^{3+}$, $Fe^{3+}$ and the like.

The synthesis of the green antimicrobial cream is summarized, in detail, as follows:

Step 1: sodium lauryl ether sulfate $(CH_3(CH_2)_{10}((CH_2)O)_nSO_3Na$, where n is 2 or Step 2: water containing natural minerals, such as Mg, Na, Ca, Fe, and the like Step 3: Brilliant Blue: $C_{37}H_{34}N_2O_9S_3$, wherein Brilliant Blue is a food colorant Step 4: 2.2 kg of NaCl, the amount of which may vary depending on the use (cosmetic vs. skin infection). In this step, the solution may be blue in color.

Step 5: adding the ingredients of Steps 1-4 together with gray clay Kaolin, which has the following formula:

$(Ca,Na,H)(Al,Mg,Fe,Zn)_2(Si,Al)_4O_{10}(OH)_2*H_2O$

After mixing the ingredients, the gray color will change to green, wherein the final product is the antimicrobial green clay cream having the following formula:

$(Al, Zn, Fe_1, 67MgO_{33})Si_4O_{10}(OH)_2Na^+Ca^{++}$

In more detail, during Step 5 the green clay reacts as Bronsted character, and the materials react to the balance and stability of every element in an antimicrobial concept. The hydrogen protons ($H^+$) are attracted to the negatively charged clay surface to varying degrees, as shown below:

$[M(H_2O)_n]^{3+} \leftrightarrow [M(H_2O)_n1OH]^{2+}+H^+$, where green cream clay has a pH of 7.4

Thus, the change to a green color is justified by the transformation of $Fe^{2+}$ to $Fe^{3+}+e$. In other words, the color of the product, the antimicrobial clay, is becoming green because of the combination of the two forms of iron. Thus, the antimicrobial green clay is the product of mixed valence condition of formation. The iron is reduced from $Fe^{3+}$ and enters into a silicate mineral structure. In general, iron would rather be an oxide when it is in the trivalent state, at which time it is reduced to the divalent state under the surface or near the surface. The silicate, sulfide, or carbonate hides when the silicate is oxidized, and the iron begins to group together in oxide clumps, eventually exiting the silicate structure. The production of trivalent oxidized iron typically results in a yellow, brown, or orange color. However, with the presence of Brilliant Blue or Blue Tartrazine, the color becomes green. The resulting final product has the following chemical structure: $(Al,Zn,Fe1,67MgO,33)Si_4O_{10}(OH)_2Na^+Ca^{++})$.

Use of the Product for Skin Regeneration:

In the regeneration process of skin, calcium may be very important. Calcium has an established role in the homeostasis of mammalian skin and serves as a modulator in Keratinocyte proliferation and differentiation. Gradients of calcium concentrations increasing from 0.6 mM in the basal layer to >1.4mM in the stratum granulosum are consistent with migration patterns in response to minor abrasions (normal wear). Dermal fibroblasts require calcium, but are approximately 100 times less sensitive than Keratinocytes. Normal calcium metabolism in the skin is dependent on cell membrane and cytosolic calcium binding proteins (calmodulin, cadherins, etc.). In wound repair, calcium is predominantly involved as Factor IV in the hemostatic phase, but it is expected to be required in epidermal cell migration and regeneration in later stage healing. Calcium is a potential central regular in wound healing. Also, a sustained elevated intracellular calcium ($Ca^{2+}$) concentration has thus emerged as a universal and require characteristic of activated cells. Activation of stem cells by $Ca^{2+}$ was accomplished by the use of the antimicrobial green clay cream of the present disclosure.

In the antimicrobial cream of the present disclosure, the role of $Ca^{2+}$ in stem cell activation suggests that the cells use the intracellular $Ca^{2+}$ concentration as a gauge to respond dynamically to the multitude of signals vying for their attention. Stem cells may adjust their proliferation activity in response to a wider variety of $Ca^{2+}$ signals. Thus, the extra concentration of calcium may emerge as a master regulator of stem cell activity. In other words, the $Ca^{2+}$ level in the antimicrobial cream may regulate stem cell activity (such as L-glutamate activity) by triggering a sustained increase of $Ca^{2+}$ within the cell. It should be noted that this change is not limited to the response to L-glutamate.

In the process of healing a wound or burn with the antimicrobial cream, the cells may acquire the molecules and ions needed from the area surrounding the cells. Thus, there may be an increased traffic of molecules and ions in and out of the cells through their plasma membrane. In healing wounds and skin regeneration, two problems should be considered:
(1) Relative concentrations of molecules and ions, and ions moving spontaneously down their concentration gradient diffusion
(2) Lipid layers are impermeable to most essential molecules and ions. The bilayers are permeable to water molecules and few other small, uncharged molecules, like oxygen ($O_2$) and carbon dioxide ($CO_2$, which may diffuse into or out of the cells through the plasma membrane in a process referred to as osmosis. However, lipid bilayers are impermeable to $K^+$, $Na^+$, $Ca^{2+}$, $Cl^-$, and $HCO_3^-$.

Small hydrophilic molecules, such as glucose, and molecules, like proteins and RNA, can be transported into cells by the facilitation of ligand transmembrane proteins. For example, the direct active transport with $Na^+/K^+$ATPase is established by the active transport of both ions. Specifically, cytosol in human cells contains a concentration of potassium ions ($K^+$) that is as much as 20 times higher than in the extracellular fluid, and the extracellular fluid contains a concentration of $Na^+$ as much as 10 times greater than within the cell. By the known sodium potassium pump mechanism, three $Na^+$ ions are actively transported out of the cell for every 2 $K^+$ ions pumped into the cell. This process helps establish a net charge across the plasma membrane with the interior of the cell being negatively charged with respect to the exterior. The resting potential may prepare nerve and muscle cells for the propagation of action potentials leading to nerve impulse and muscle action.

Normally, accumulation of sodium ions outside of the cells draws out the cells ability to maintain osmotic balance, wherein the gradient of sodium ions is harnessed to provide the energy to run several types of indirect pumps. The importance of the roles of $Na^+/K^+$ATP may be reflected in the fact that almost ⅓ of all energy from mitochondria in human cells is used to pump. In the healing process, the antimicrobial cream of the present disclosure may help human cells regulate osmosis balance by the presence of both Brilliant Blue and sodium laureth sulfate, while also assuring stability by the balance of $Na^+$ ions in fixing the $Ca^{2+}$ ions. $Zn^{2+}$, $Fe^{2+}$, $Fe^{3+}$, and $Al^{3+}$ may act as pumps, attracting $Na^+$ and providing the necessary ions for regeneration of damaged cells to wounds, burns, infections, and the like, while ensuring harmony and normal cellular function.

$Ca^{2+}$/ATPase: $Ca^{2+}$/ATPase is located in the plasma membrane of all eukaryotic cells, which use the energy provided by one molecule of ATP to pump $Ca^{2+}$ ions in and out of the cell. This activity helps to maintain concentration gradients between the cytosol and outside of the cell. During the process of healing rounds and burns, all elements, vitamins, and minerals, including $Ca^{2+}$ may be beneficial to regenerate cells. In the green antimicrobial cream of the present disclosure, calcium is present, as evidenced by the chemical structure of the final product.

The Role of Silicon Contained in the Green Clay Cream

Silicon may allow molecular structures to be established and the metabolism to function. Specifically, silicon may be necessary for the synthesis of collagen, elastin, and hyaluronic acid. Thus, silicon may influence the formation of connective tissue, including cartilage, bone, and skin, and may improve a body's immunity. The silicon may initiate the growth and regeneration of cells and body structures. In elastin and collagen, silicon may protect the vascular wall, veins, and arteries. With respect to the skin, the silicon may act as the dermis that the epidermis finds itself attached to.

Silicon may also play a role when it comes to the immune system and hormones. As mentioned above, silicon may be essential for formation of the skin, joints, nails, and hair and, thus, its presence may improve healing, which improves the immune system, maintains flexibility, and strengthens blood vessels. Silicon's presence may also prevent aging and inflammation. Silicon may also help with electrical connections in the brain and other areas of the body. Because silicon is such a prevalent and beneficial element, the green cream clay that contains silicon may help regenerate skin in wounds, burns, and ulcers.

Moreover, silicon is tetravalent, meaning it may be able to create hydrogen bonds with nitrogen and oxygen in wounds, allowing it to react with molecules containing these two elements. The silicon may thus consolidate the structure or promote the enzymatic catalysis of certain molecules, such as collagen, elastin, phospholipids, and structural proteins, such as hyaluronic acid and glucosamine.

The skin cream of the present disclosure may, therefore, comprise an antimicrobial, kaolinite and montmorillonite green cream clay composition with weak acids (fatty acids), oleic acids, benzoic acids, clove oil (C5, C14 antimicrobial properties and anti-aging abilities and properties), trace elements, vitamins, and mineral elements. The final skin cream may provide the ability and function of healing skin disease, Buruli ulcers, wounds, and burns without spots or scars. In some embodiments, the cream may be used with poultice and compresses for burns and deep wounds.

Antimicrobial Abilities of the Cream of the Present Disclosure

Lauryl ether sulfate and Brilliant Blue or Blue Tartrazine may be beneficial in the process of wound healing, and they may have antimicrobial properties. Specifically, these molecules may provide for polystyrene cation exchange. Sodium polystyrene effects the exchange of sodium and potassium in the body. Sodium polystyrene sulfonate may be used to treat high levels of potassium in the blood, also called hyperkalemia. In the cream of the present disclosure, the ions present in the product may exchange the cations necessary for skin regeneration, wound healing, and treating skin infections by creating an antimicrobial compound (zin coceth sulfate, magnesium coceth sulfate) and introducing the ions necessary to reactivate and regenerate damaged cells in the wound or infection.

Hard metal and heavy metal ions ($Ca^{2+}$, $Zn^{2+}$, $Mg^{2+}$, $Fe^{3+}$, $Fe^{2+}$, $Al^{3+}$, and the like) are contained in the cream of the present disclosure. Sodium ($Na^+$) may be considered a weak or soft metal ion and is contained in the lauryl ether sulfate and Brilliant Blue or Blue Tartrazine. Like polystyrene sulfonate, lauryl ether may exchange its sodium ion and capture a heavy metal contained in the gray clay during the synthesis process, acquiring the antimicrobial properties described above. An exemplary compound that may be formed during the synthesis of the cream of the present disclosure is zinc coceth sulfate, the structure of which is shown below:

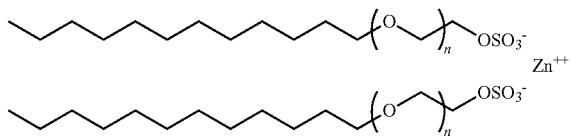

Zinc coceth sulfate may be obtained by cation exchange including the migration of a heavy metal into polystyrene sulfonate, wherein the weak ion (sodium in the sodium ether lauryl sulfate) may be displaced by the polystyrene sulfonate and captured by the zinc ions contained in the clay.

Zinc coceth sulfate may be useful for treating skin disorders associated with *Propionibacterium acnes*.

The synthesis of zinc coceth sulfate is shown below:

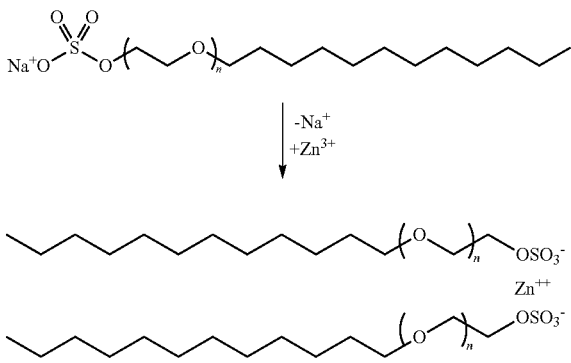

Another exemplary compound that may be formed is magnesium coceth sulfate, the structure of which is shown below:

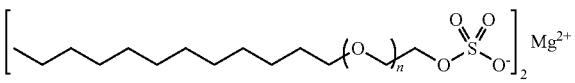

Magnesium coceth sulfate has antimicrobial properties and may be important in the treatment of skin infections, particularly when a person has a large wound or poor skin restoration abilities due to diabetes, psoriasis, leprosy, and Buruli Ulcers. The magnesium binds calcium and is involved in calcium metabolism on the parathyroid glands. At the cellular level, it controls and regulates the entry of calcium into the cell and intracellular fluids.

Magnesium may inhibit cation channels, such as sodium and calcium receptors, and may act as a calcium antagonist. It may thus protect mitochondria against calcium overload. In the wound healing process, magnesium may play primarily an intracellular role. Also, formed is $MgCl_2$. The $MgCl_2$ present in the composition of the present disclosure may allow damaged cells to regain their phagocytic power in a large proportion.

Polystyrene Exchange Process

The exchange process may be performed by lauryl ether sulfate and brilliant blue, which may act as pump membranes with the ability to displace soft or weak metals by fixing hard metals in the damaged cells, wherein the hard metals may help with cell regeneration. They may also act as a barrier between the heavy metal and the sodium ion by establishing the barrier and controlling the flux of ions (mainly sodium) in the body. The barrier may help to fix ions ($Ca^{2+}$, $Mg^{2+}$, $Mn^{2+}$, $Fe^{2+}$, and $Fe^{3+}$) in the human body with the purpose of wound healing and treating skin infections. Moreover, they may act as a regulator of osmosis activity between extra and intra cells by maintaining flux of important mineral elements through damaged cells (wounds, burns, skin infections, etc.). They may additionally act to rehabilitate skin minerals in the case of alopecia treatment, and to rejuvenate the skin and help prevent or combat wrinkles, and, finally, to prevent sodium ions from penetrating into cells and manage osmotic pressure between the intra and extra cellular environment, balancing the pressure within the cells.

In the composition of the present disclosure, the polystyrene exchanges the heavy metal by displacing $Na^+$, creating more antimicrobial compounds, which may be helpful in healing wounds and skin infections. Many new compounds may be formed by the exchange of sodium ions. The compounds also include calcium coceth sulfate, magnesium coceth sulfate, zinc coceth sulfate, iron coceth sulfate, potassium coceth sulfate, and the like. The structures of these compounds are shown below:

Calcium coceth sulfate:

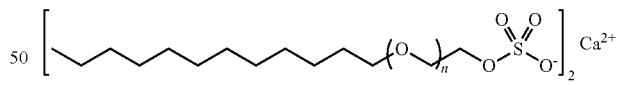

Magnesium coceth sulfate:

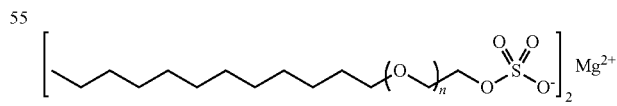

Zinc coceth sulfate:

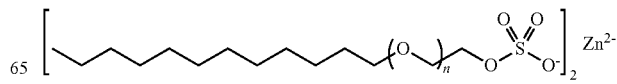

Iron (ii) coceth sulfate:

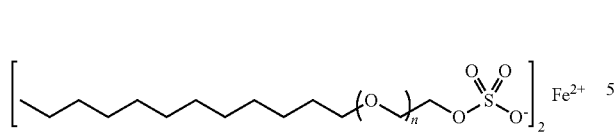

Iron (iii) coceth sulfate:

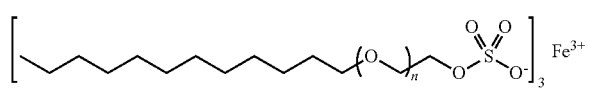

Potassium coceth sulfate:

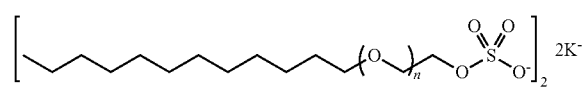

Aluminum coceth sulfate:

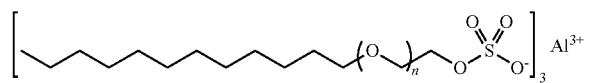

The exchange processes are outlined below, wherein Brilliant Blue or Blue Tartrazine is the polystyrene sulfonate.

The antimicrobial compound may also include $Ca^{2+}$ ions as a result of calcium chloride. $Ca^{2+}$ intracellular processes may enhance wound healing and skin disease therapy:

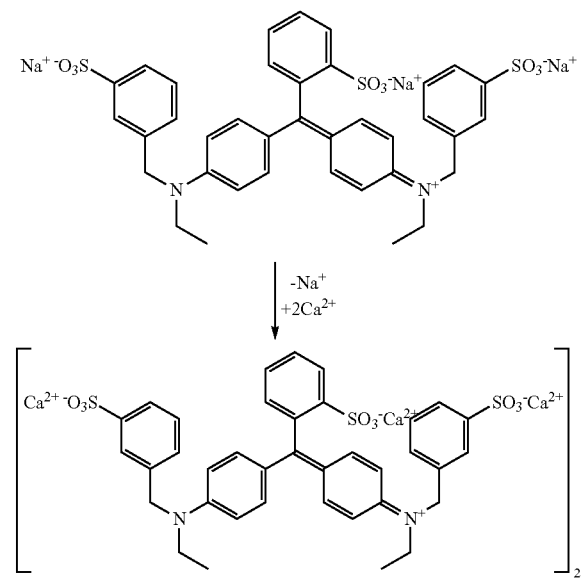

The antimicrobial compound may include magnesium via a reaction with magnesium chloride, wherein $Mg^{2+}$ may improve wound healing and skin disease therapy.

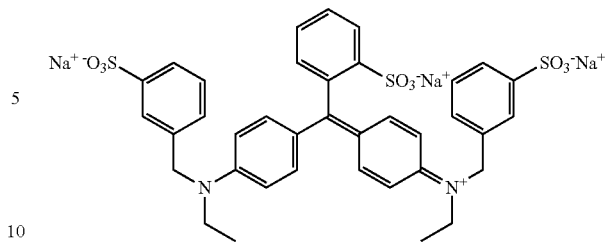

The antimicrobial compound may include zinc ions, wherein $Zn^{2+}$ may improve intracellular processes involved in wound healing and skin disease therapy.

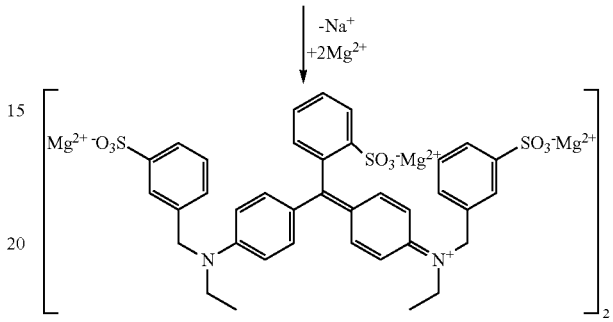

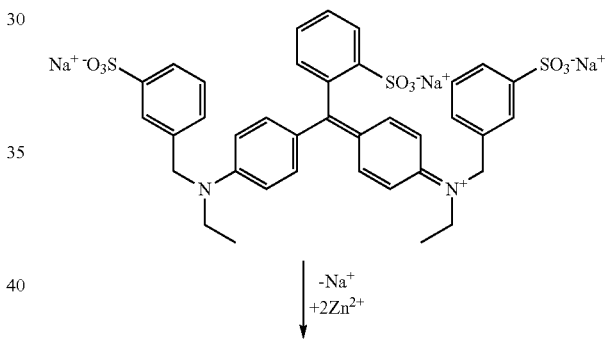

The antimicrobial compound with iron (II) may improve intracellular processes involved in wound healing and skin disease therapy, because iron may play a key role in both oxidative stress and photo-induced skin damage. Iron may be considered a vital co-factor for proteins and enzymes involved in energy metabolism respiration DNA synthesis. Iron may have a specific function, such as the metabolism of collagen by procollagen-proline dioxygenase.

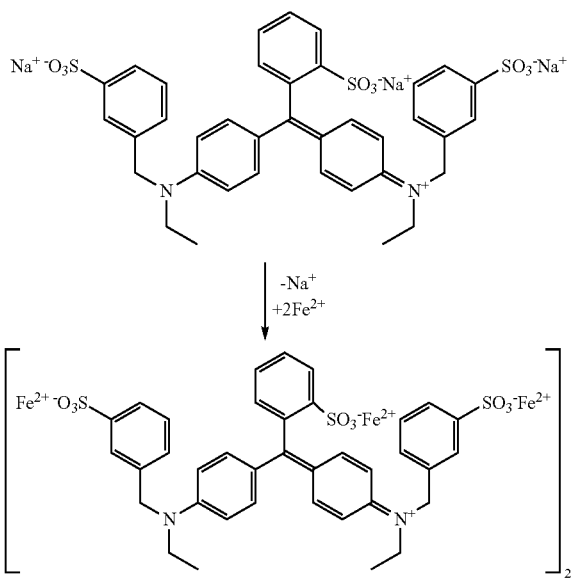

The antimicrobial compound may include iron (III) ions, which may improve intracellular processes involved in wound healing and skin disease therapy, wherein iron is a transition metal that may exist in two stages: $Fe^{2+}$ and $Fe^{3+}$. Intracellular labile may undergo redox cycling between its two most stable oxidations states and react as a superoxide anion with hydrogen peroxide giving hydroxyl radicals. In this process, iron (II) and iron (III) may be used to transport oxygen or catalyze electron transfer reactions, nitrogen fixation, or DNA synthesis.

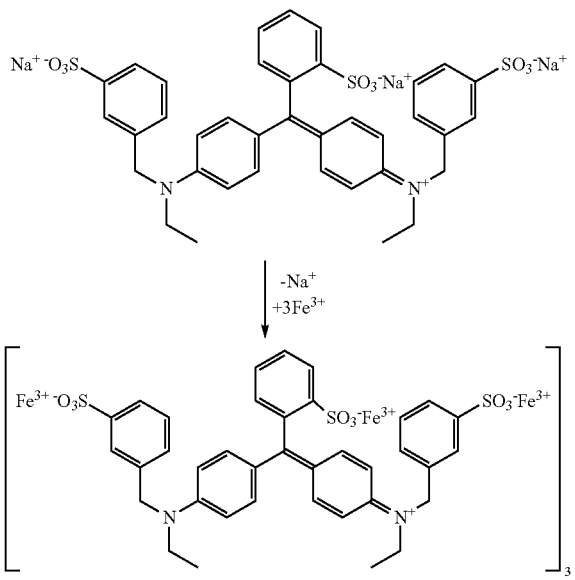

The antimicrobial compound may include potassium ions, wherein $K^+$ may improve intracellular processes involved in wound healing and skin disease therapy. In the present disclosure, the sodium does not penetrate the cells because of two barriers—the heavy metal with the pump polystyrene sulfonate and $Na^+/K^+$ ATP. Actively, there are 3 $Na^+$ transported out of the cell for every 2 $K^+$ pumped into the cell. This process helps establish a net charge across the plasma membrane with the interior being negatively charged with respect to the exterior.

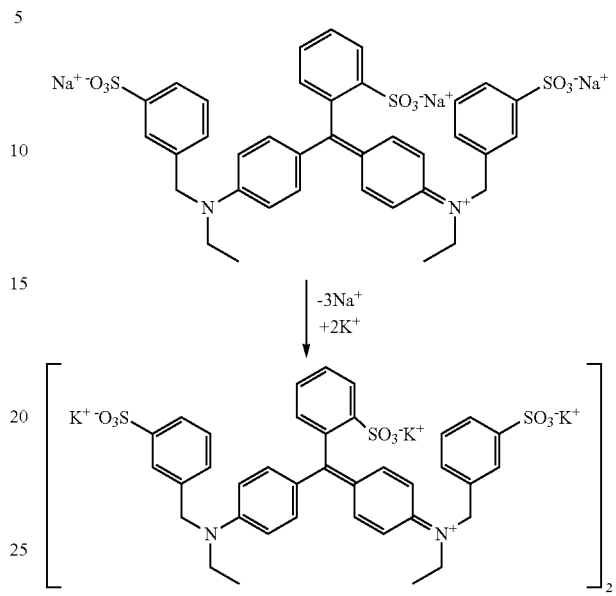

The antimicrobial compound may also include $Al^{3+}$ ions, wherein there may be a correlation between silicon and aluminum ions. Silicon and aluminum $[AlSiO_4]^-$, $(SiO_2)$ may provide stability in a biological environment. Silica may increase the anti-inflammatory capabilities under the control of aluminum. In the wound healing process, silicon may extract abnormal aluminum proteins in damaged cells and, thus, help accelerate skin regeneration. In the composition of the present disclosure, aluminum together with silicon may help initiate and regularize the immune system in wounds, burns, and skin lesions. Silicon may reduce or regulate the multiplication of fibroblasts in the healing process of wounds, burns, lesions, and skin regeneration.

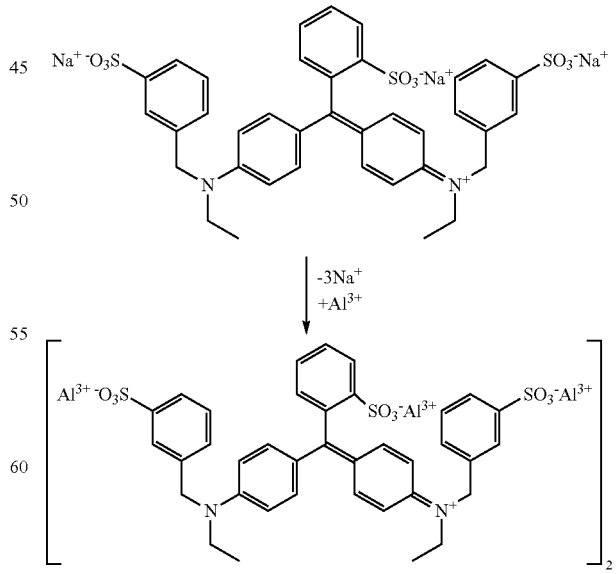

When it comes to magnesium coceth sulfate, magnesium chloride may activate the phagocytic leukocyte. Thus, magnesium chloride in the cream of the present disclosure may allow damaged cells to regain their phagocytic power in a proportion of about 300%. Thus, the magnesium chloride may help with the wound healing process.

The human body requires essential heavy metals, include Cu, Zn, Mg, and Ca, to carry out biological functions. In the biological system, the metals are mostly bound to proteins. The metalloproteins have both catalytic and structural roles, such as the following: (i) as a constituent of enzyme active sites; (ii) for stabilizing enzyme tertiary or quaternary structure; (iii) for forming weak bonds with substrates, contributing to their orientation to support chemical reactions; and (iv) for stabilizing charged transition sites. Cu, Fe, and Mn have an impaired (or unpaired) electron that allows for their participation in redox reactions, such as those at enzyme active sites.

Mn has unpaired electrons that allow for its participation in redox reactions at enzyme active sites. Cu mediates the reduction of one superoxide anion to hydrogen peroxide and oxidation of a second superoxide anion to molecular oxygen in the active site of cytoplasmic superoxide mutations. Zn has no unpaired electrons in $Zn^{2+}$ and it may prevent the formation of harmful free radicals by competing with the redox active metals, such as Fe and Cu, at the enzyme active sites. The heavy metals may be immediately complexed with molecules or peptides upon entry to the cell.

Biological Function of Lauryl Ether Sulfate and Brilliant Blue

In the antimicrobial composition of the present disclosure, the presence of sodium laureth sulfate and brilliant blue or blue tartrazine react like a pump membrane and as a barrier between heavy metals and sodium ions by establishing barrier and control the flux of ions in the human body, mainly the sodium ion. This barrier may help fix ions in the human body for wound healing and treating skin infections. It may also react as a regulator of osmosis activity between intra and extracellular by maintaining flux of important elements through damaged cells in skin regeneration and the treatment of skin diseases. It may also rehabilitate mineral elements of the skin in the case of, for example, alopecia treatment. It may also rejuvenate skin and help prevent wrinkles and help the skin remineralize. Lastly, it may penetrate into cells and manage the osmotic pressure for the balance of pressure within cells.

Biological Function of Sodium Chloride or Sodium Ions

Sodium does not penetrate the cells because of the barrier created by the heavy metal. Thus, the sodium in the composition of the present disclosure does not penetrate the protective membrane. As a result, a net charge is established across the plasma membrane with the interior being negatively charged with respect to the exterior. The accumulation of salt outside of the cells may help maintain osmotic balance of the sodium gradient. The osmotic balance may be fixed by the polystyrene membrane by fixing heavy metal ions into the cells and displacing sodium ions. Finally, sodium ions do not have any biologic function in the wound healing process and skin disease treatment. Rather, the sodium chloride may soften the bond in the composition of the present disclosure. The salt in the cream of the present disclosure may have a cosmetic functions, helping to effectively clean the skin.

Certain molecules and salts included in the composition of the present disclosure may promote the healing of wounds and burns without spots and scars. Those salts include, for example, acidified sodium chloride (NaCl→ $Na^+$, $Cl^-$), zinc coceth sulfate, magnesium coceth sulfate, potassium coceth sulfate, calcium coceth sulfate, aluminum coceth sulfate, and aluminum chloride ($Al^{3+}$, $Cl^- \to {}^{AlCl}_3$).

Correlation between Silicon and Aluminum

In the composition of the present disclosure, there may be a correlation between silicon and aluminum reactivity. The correlation demonstrates the link of both elements. Thus, silicon prefers coordination numbers with a tetrahedral atomic environment, while aluminum prefers octahedral coordination in hydrated cations, oxides, hydroxides, and coordination complexes. The isoelectric relationship between $(SiO_2)_2$ and $[AlSiO_4]_-$ may be the foundation of vast aluminosilicate chemistry.

In the case of a clay mineral, this correlation may be:

$$2Al(OH)a(c)+2H_4SiO_4(aq) \to Al_2Si_2O_5(OH)_4+5H_2O$$

$$Al_2Si_2O_5(OH)_4+6H+2Al+2H_4SiO_4(aq)+H_2O$$

The presence of $Al^{3+}$ may react with to create aluminum chloride to stimulate skin regeneration and wound healing.

The green tea in the cream of the present disclosure may help fight inflammation. The salt may have strong cleansing properties. The talc may be a mineral comprising hydrated magnesium silicate ($H_2Mg_3(SiO_3)$ or $Mg_3SiO_{10}(OH)_2$. The menthol ($C_{10}H_{19}$ OH) may relieve minor aches and pains. Clove oil may be used for its antiseptic properties. Additionally, it contains eugenol, which has anti-bacterial properties; thus, the clove oil may help clear cystic acne and kill infections, thus reducing swelling. Olive oil may help fight signs of aging. The honey used in the cream of the present disclosure may be a saturated or super saturated solution of sugars. The honey may be diluted by wound exudates, creating hydrogen peroxide via a glucose oxidase enzyme reaction and resulting in antibacterial activity that does not damage the tissue.

The vitamins included in the cream may have various purposes. For example, vitamin A may help rebuild tissue by playing a role in the development of lymphocytes, which are cells that fight off bacteria and disease. Vitamin D may contain effective antioxidants that help fight free radicals in the body. Vitamin C may provide potent antioxidant protection, healing the skin from damage from free radicals, may boost healthy collagen production, may reduce the appearance of brown spots and other sun damage, may reduce inflammation and irritation, may fade post-breakout red marks, and may increase the effectiveness of sunscreens. Vitamins B2 may promote metabolism and mobilize iron from storage to incorporate into cells. Vitamin B6 may help utilize the energy contained in food and is important for carbohydrate, protein, and fat metabolism.

The cream of the present disclosure may have a clay-like consistency, wherein the ingredients of the cream may stimulate the regeneration of skin cells. Thus, facials masks and exfoliating scrubs made with the cream may result in the stem cells located within the skin actively generate differentiating cells that may ultimately form either the body surface or the hairs that emanate from it. The stem cells may be able to replenish themselves, continually rejuvenating the skin and hair.

In some embodiments, the cream may be synthesized using a 3-phase process: (1) creating an anti-microbial colloid liquid, which may be blue; (2) creating an anti-microbial solid, which may be green; and (3) creating an anti-microbial, creamy, gelatinous solid and vitamin, which may be green. Mixing of the cream may be done with a mixer coated with a plastic material. This specific type of mixer may be needed because the skin cream is rich in mineral elements, trace elements, weak acids, and vitamins. Examples of each step are described below.

Example 1: Creating the Anti-Microbial Colloid Liquid 2.2 kg of salt were mixed in a phase manner with water. Sodium lauryl ether sulfate and 0.6 oz (or 18 g) of blue tartrazine were mixed in with the salt water, creating the anti-microbial colloidal solution having a blue color.

Example 2: Creating the Anti-Microbial Solid

The colloidal blue anti-microbial solution prepared in Example 1 was mixed with 25 L olive oil; 25 L clove oil; 20 L honey; 5 L green tea; 10 L aloe vera; a 260 kg mixture comprising kaolin gray, phyllosilicates, and aluminum silicate hydrates; 20 kg of talc; and 20 L of mineral oil. The solution was mixed thoroughly using a plastic coated blender, resulting in a green clay cream. It could have alternatively been mixed using just a plastic mixing spoon.

Example 3: Creating the Anti-Microbial, Creamy, Gelatinous Solid 95 kg of gelatin was slightly warmed to about 40° C. with 100 g of menthol to create a diluted solution. The amount of gelatin may be changed to change the viscosity of the skin cream. In embodiments, the gelatin may be added as a granular powder, which would swell when stirred into water. When dry gelatin is used, it may be used in an amount such that a water/gelatin mixture would not exceed about 34% gelatin. While warming, the gelatin solution may be allowed to hydrate for about 30 min. The diluted solution was poured into a mixing bowl. The green clay cream from Example 2 was then mixed into the mixing bowl. While the composition is being blended, it was simultaneously cooled to about 37° C. After cooling, vitamins are added to the mixture, which is then mixed again, creating antimicrobial green cream Kaolin clay, gelatinous and bright (the cream of the present disclosure).

The resulting cream includes silica, aluminum, calcium, and potassium as major elements and copper, lithium, molydedenum, and cobalt as minor elements. Some embodiments of the cream have a formula represented by $(Al,Zn,Fe_1,67MgO_{33})Si_4O_{10}(OH)_2Na^+Ca^{2+}$ plus weak acids, such as benzoic acid, fatty acids, such as ascorbic acid, vitamins, and an antimicrobial agent. The mineral content of the product may vary due to the impurities.

The cream has anti-microbial and antibiotic properties and comprises trace elements, minerals, protein, polypeptides, and a weak acid, such as benzoic acid, which may give the cream its anti-aging and anti-microbial properties.

To use the cream of the present disclosure, a user may apply it externally on the skin or internally. When the cream is applied to the skin, transduction may occur, causing physical energy to be converted into energy used by the nervous system and reducing tension and anxiety in a user. For large wounds and burns, the cream may be gently rubbed on the wound or burn and covered with a compress when dry. The pain may be inhibited and the wound may heal without forming a scar. The cream may be removed from the body after the wound is healed by hydrotherapy, which may eliminate toxins.

The cream of the present disclosure may clean the skin of all or substantially all impurities, such as acne, spots, dead, skin fat, and the like. The cream may also have the ability to clean the face, heal most skin blemishes, whitlow, boils, ringworm, burns, stings, lesions, and the like. The cream may also be able to curb the proliferation of parasites, harmful bacteria, and microbes. The cream may also drain impurities, such as puss, from fabric, as the cream absorbs excess liquid and neutralizes the actions of various alkaloids. Moreover, the cream may have the ability to clean the blood and lymphatic system. The cream may also reinforce defenses, revitalize organs, neutralize poisons, strengthen bones, and reduce inflammation. In some embodiments, the cream may be used to nourish the scalp in cases of alopecia.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A cream for treating the skin, the cream comprising:
   gray clay kaolin;
   sodium lauryl ether sulfate; $CH_3(CH_2)_{11}(OCH_2CH_2)_n OSO_3Na$, where n is from about 2 to about 3;
   blue tartrazine, $C_{16}H_9N_4Na_3O_9S_2$;
   sodium chloride;
   menthol;
   metabisulfite sodium;
   gelatin;
   mineral oil;
   olive oil;
   oil of cloves;
   water;
   green tea;
   talc;
   honey; and
   aloe vera,
   wherein:
      a weight ratio of blue tartrazine to gray clay kaolin is about 0.00007:1;
      a weight ratio of salt to gray clay kaolin is about 1:118; and
      a weight ratio of talc to gray clay kaolin is about 1:13.

2. The cream of claim 1, further comprising perfume.

3. The cream of claim 1, further comprising a mixture of vitamins.

4. The cream of claim 3, wherein the mixture of vitamins comprises vitamin E, vitamin C, vitamin B2, vitamin B5, vitamin H, vitamin B6, and vitamin D.

5. The cream of claim 1, further comprising apple perfume, vitamin E, vitamin C, vitamin B2, vitamin B5, vitamin H, vitamin B6, and vitamin D.

6. The cream of claim 5, wherein a batch of the cream comprises:
   about 260 kg gray kaolin clay;
   about 4 kg sodium lauryl ether sulfate;
   about 0.6 oz blue tartrazine;
   about 2.2 kg sodium chloride;
   about 100g menthol;
   about 50 g metabisulfite sodium;
   about 95 kg gelatin;
   about 20 L mineral oil;
   about 25 L olive oil;
   about 25 L oil of cloves;
   about 20 L water;
   about 20 kg talc;
   about 5 L green tea;
   about ⅛ L perfume;
   about 5 L honey;
   about 10 L aloe vera;
   about 2,000 international units (IU) vitamin E;
   about 100,000 IU vitamin A;
   about 300 mg vitamin C;
   about 100 mg vitamin B2;
   about 250 mg vitamin B5;
   about 2.5 mg vitamin H;
   about 100 mg vitamin B6; and
   about 400 IU vitamin D.

7. The cream of claim 1, wherein the cream comprises about 60% gray clay kaolin.

8. The cream of claim 1, wherein the cream has a pH of about 7.4.

* * * * *